Figure 1:
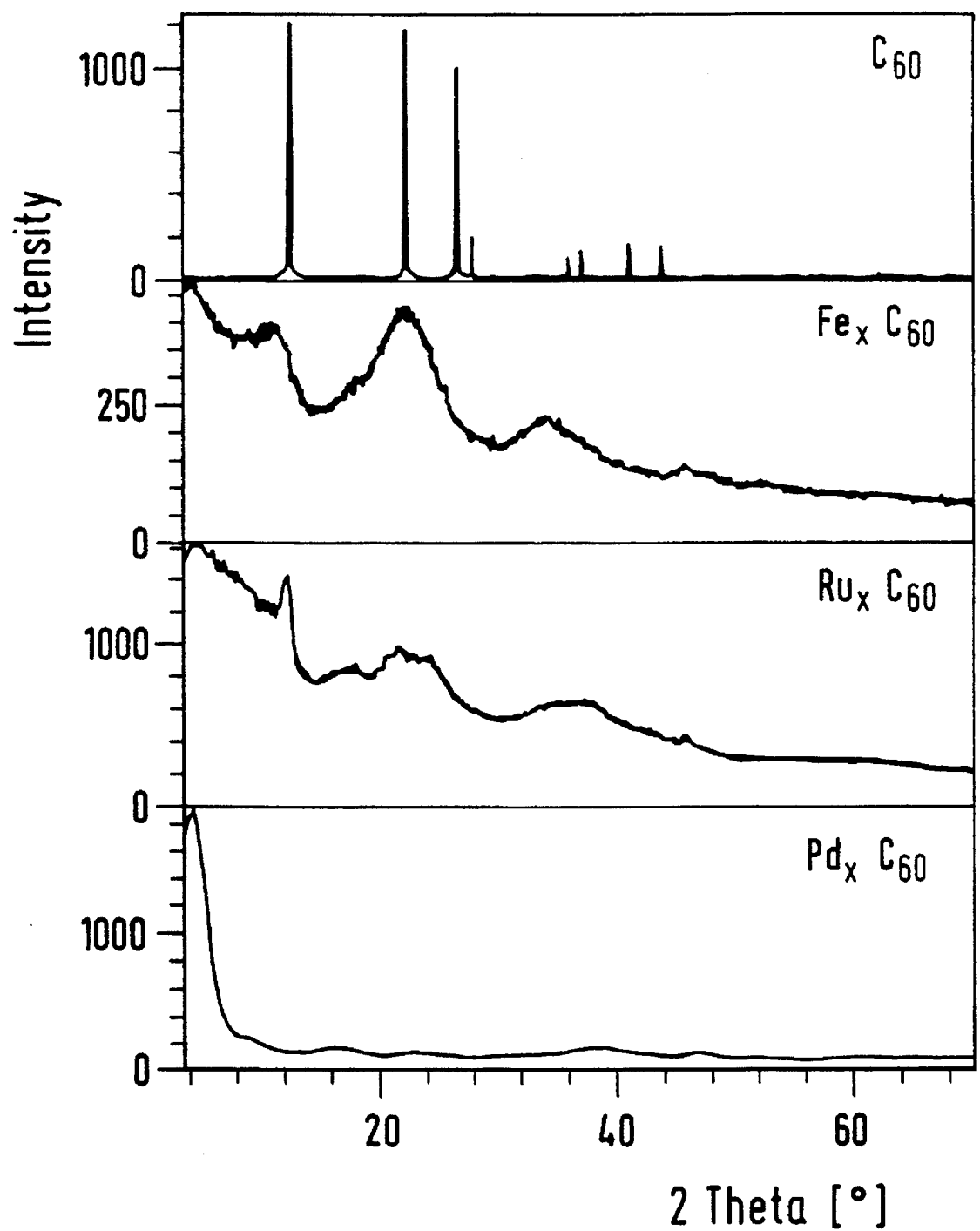

United States Patent [19]
Schlögl et al.

[11] Patent Number: 5,523,438
[45] Date of Patent: Jun. 4, 1996

[54] METAL-FULLERENE INTERCALATION COMPOUNDS, PROCESS FOR THEIR PREPARATION AND USE AS CATALYSTS

[75] Inventors: Robert Schlögl, Frankfurt; Harald Werner; Michael Wohlers, both of Eschborn, all of Germany

[73] Assignee: Hoechst Aktiengesellschaft, Germany

[21] Appl. No.: 279,252

[22] Filed: Jul. 21, 1994

[30] Foreign Application Priority Data

Jul. 23, 1993 [DE] Germany .......................... 43 24 693.1

[51] Int. Cl.⁶ ..................................... C07F 15/00
[52] U.S. Cl. ........................... 556/136; 556/141; 556/142; 556/146; 556/148
[58] Field of Search .................................. 556/136, 141, 556/142, 146, 148

[56] References Cited

U.S. PATENT DOCUMENTS 5,300,203  4/1994  Smalley .............................. 204/157.41

FOREIGN PATENT DOCUMENTS

WO93/22239  11/1993  WIPO .

OTHER PUBLICATIONS

Derwent Abstract No. JOP5327038 published Dec. 10, 1993.

Hawkins et al., J. Org. Chem., vol. 55, pp. 6250–6252 (1990).

Chemical Abstract, vol. 121, No. 8, Aug. 22, 1994, Abstract No. 121:98265e entitled "Synthesis and characterization of transition metal fullerides".

Chemical Abstract, vol. 121, No. 8, Aug. 22, 1994, Abstract No. 121:967052 entitled "Fullerene Intercalation Compounds".

*Primary Examiner*—Porfirio Nazario-Gonzales
*Attorney, Agent, or Firm*—Curtis, Morris & Safford

[57] ABSTRACT

Metal-fullerene intercalation compounds, process for their preparation and use as catalysts Transition metal-fullerene intercalation compounds and a process for the preparation thereof by reaction of transition metal compounds with fullerenes or fullerene-containing carbon black with activation in a solvent.

21 Claims, 3 Drawing Sheets

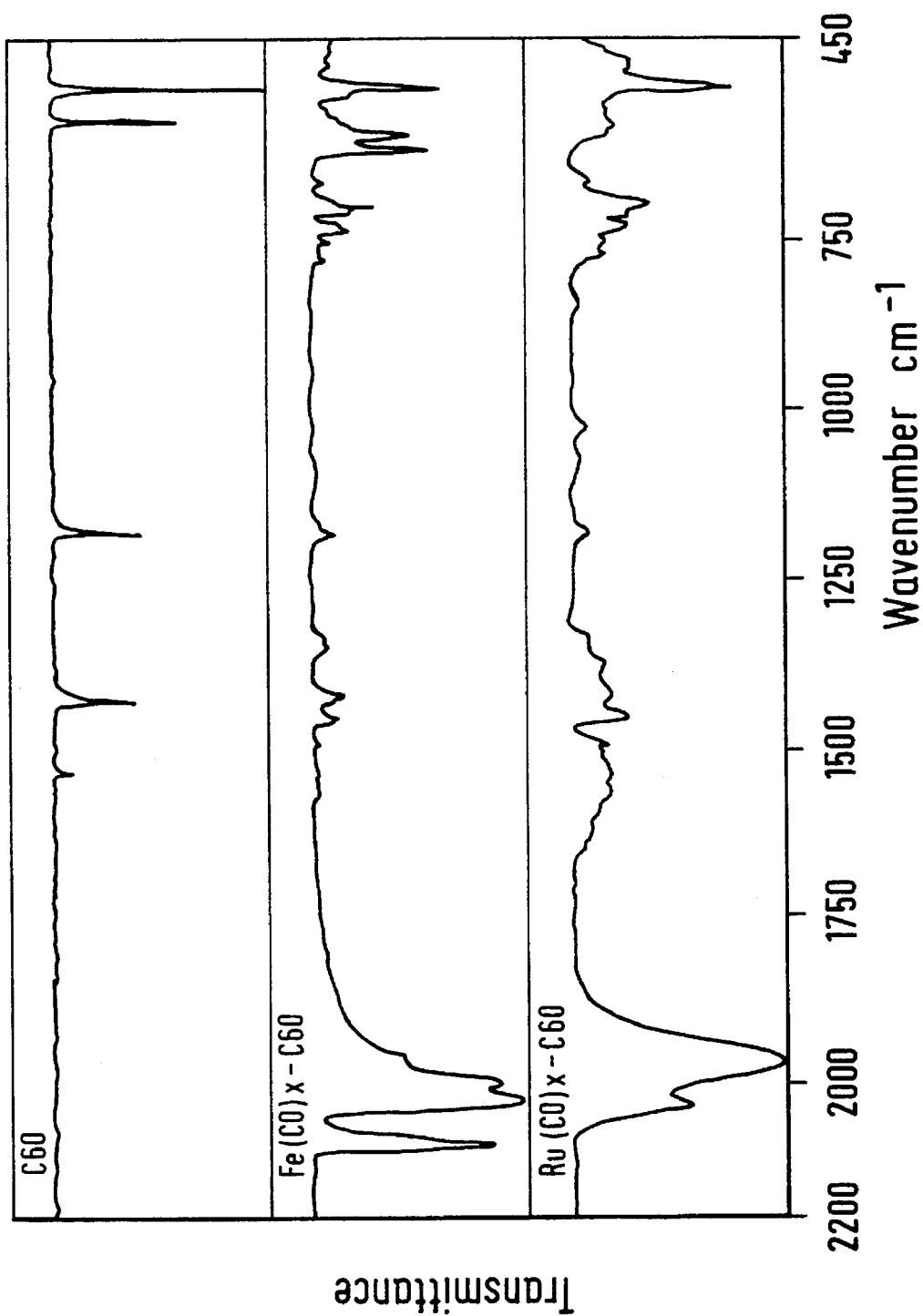

METAL-FULLERENE INTERCALATION COMPOUNDS, PROCESS FOR THEIR PREPARATION AND USE AS CATALYSTS

The preparation of metal-fullerene complexes, such as the synthesis of the hexakisdiethylphosphinoplatinum-$C_{60}$ complex and the syntheses of bis(triphenylphosphino)platinum-$C_{60}$ and of pentamethylcyclopentadieneruthenium-$C_{60}$ oligomers, is described by Fagan et al. (J. Am. Chem. Soc. 1991, 113, 9408; Science, 1991, 252, 1160; J. Am. Chem. Soc., 1989, 111, 1698).

The production of Fe—$C_{60}$ complexes was carried out by Fraser et al in ion-beam experiments (J. Am. Chem. Soc., 1992, 114, 2726) starting from $C_{60}+$ and iron pentacarbonyl. Other metal-fullerene cations were likewise produced in a mass spectrometer (J. Am. Chem. Soc., 1991, 113, 8186; ibid 1991, 113, 6298; ibid 1991, 113, 9418). In essence, the clusters thus obtained were not isolated, since this preparative method is not suitable for the preparation of relatively large amounts of metal-fullerene complexes. Owing to the high reactivity of the intermediates, the compounds obtained are also unsuitable as catalysts.

Rao and co-workers (J. Am. Chem. Soc., 1992, 114, 2272; Ind. J. Chem., 1992, F17) describe the preparation of iron-fullerene complexes in which the iron atom is said to be localized in the interior of the fullerene structure. Rao et al. also describe the synthesis of other undefined iron-fullerene complexes whose structure is, however, not given, but which, in analogy with the corresponding graphite compounds, are not a fullerene-iron compound, but are two-phase or three-phase mixtures of iron and/or iron chloride and amorphous fullerene.

Three studies describe compounds of osmium tetroxide ($OsO_4$) with $C_{60}$ which are stabilized by pyridine ligands on the osmium atom (Hawkins et al., Science, 1992, 252, 312; Hawkins et al., J. Org. Chem., 1990, 55, 6250; Hawkins et al., J. Am. Chem. Soc., 1992, 114, 7954). The preparation of these osmium tetroxide-$C_{60}$ adducts is carried out analogously to the synthesis of adducts of electron-deficient olefins known in the literature. The studies of Hawkins and co-workers were primarily aimed at the structure determination of $C_{60}$ and opportunities for the functionalization of fullerenes.

Studies regarding the catalytic applications of metal-fullerene complexes have hitherto been mentioned only by Nagashima et al. (Chem. Lett., 1992, 1361), the authors describing the reaction of $C_{60}$ with the dipalladium tris-dibenzylideneacetone complex. The palladium-$C_{60}$ polymer obtained was not characterized in more detail. However, it can be assumed therefrom that the compound prepared has a similar structure to that of the transition metal-fullerene complexes isolated but is polymeric. The palladium-$C_{60}$ polymer shows catalytic properties as a hydrogenation catalyst, comparable to those of a Lindlar catalyst. $C_{60}Pd_n$ having n<3, in contrast, show no activity as hydrogenation catalysts (Nagashima et al., J. Chem. Soc., Chem. Commun., 1992, 377).

A disadvantage of the abovementioned and other amorphous complex compounds prepared is the uncertainty as to whether they are physical mixtures, impure compounds or various phases of metals, metal oxides and fullerenes. However, for use of metal-fullerene complexes as catalysts or catalyst precursors it is necessary, for reasons of reproducibility, for the compounds used to have a defined form.

There was therefore a great need for the defined synthesis of metal-fullerene intercalation compounds which are in the form of pure materials and can therefore be used as catalysts.

Surprisingly, it has been found that the synthesis of defined transition metal-fullerene intercalation compounds can be successfully carried out by reaction of zero-valent transition metal compounds with fullerenes in a solvent.

The invention accordingly provides

1. Defined transition metal-fullerene intercalation compounds.
2. A process for preparing defined transition metal-fullerene intercalation compounds which comprises reacting transition metal compounds in a solvent with fullerene or fullerene-containing carbon black.

Metal complexes which form metal-fullerene intercalation compounds are all zero-valent transition metal compounds or transition metal compounds which can be reduced to the zero-valent compound under the reaction conditions. The zero-valent transition metal compounds are generally used in the form of stable complexes with ligands. Examples of transition metal complexes are iron pentacarbonyl, diiron nonacarbonyl, triiron dodecacarbonyl, triruthenium dodecacarbonyl, platinum dibenzylideneacetone, palladium dibenzylideneacetone, palladium tetrakistriethylphosphine, nickel tetracarbonyl. The compounds described are, in part, commercially available in large amounts or can be prepared by simple synthesis in analogy with the literature (T. Ukai et al., I. Oranomet. Chem., 65, 1971, 253 and G. Brauer (Editor), Handbuch der präparativen Anorganischen Chemie, Vol. 3, 1814–1838, F. Enke Verlag, Stuttgart). Preference is given to using transition metal carbonyl or transition metal dibenzylideneacetone complexes.

The starting materials used for the fullerene component can be, preferably, $C_{60}$, $C_{70}$ or mixtures thereof. However, all other conceivable fullerenes or fullerene black can be used.

The fullerenes can be obtained by preparation of fullerene black in an electric arc process with subsequent extraction using a non-polar organic solvent (crude fullerenes), as described, for example, in WO 92/09289. The further fine separation can be carried out by column chromatography. Some of the fullerenes used are also commercial products.

Suitable solvents for the preparation of the compounds are those which dissolve the fullerenes at least partially, such as aromatic solvents such as benzene, toluene, xylene, ethylbenzene, chlorobenzene, dichlorobenzene, carbon tetrachloride, chloroform, dichloromethane, furan.

Suitable ligands for stabilizing zero-valent transition metals are all conceivable stabilizing ligands known in the literature. Typical examples of such ligands are carbonyls, phosphines, arsines, olefins, alkynes, nitrogen, dibenzylideneacetone and aromatics. Preferred ligands are carbonyls and dibenzylideneacetone.

The reaction can be carried out at temperatures of from −40° to 250° C., preferably from 0° to 200° C. It can also be carried out under pressure, e.g. at from 1 to 100 atm, preferably from 1 to 10 atm. Furthermore, the reaction can be carried out photochemically, e.g. in the presence of a mercury vapor lamp.

The transition metal-fullerene intercalation compounds precipitate immediately or within 7 days, preferably in from 6 to 72 hours.

This thermal or photochemical treatment completely or partially removes the ligands bound to the metals from the transition metal complexes, the transition metal-fullerene intercalation compounds being precipitated.

The transition metal-fullerene compounds of the invention, in contrast to the metal-fullerene compounds known hitherto, are not discrete complexes or polymeric transition metal-fullerene complexes and also not ionic compounds like the alkali metal fullerides. Surprisingly, the reaction of the fullerenes with transition metal (0) compounds forms novel materials which can be described as intercalation compounds.

The structures were unambiguously identified for the first time by a number of modern analytical methods. Elemental metal analysis shows that all fullerene-transition metal intercalation compounds contain additional organic material. This is present in the form of the solvent or the ligands. FIG. 1 shows the X-ray powder diffraction patterns of the transition metal-fullerene intercalation compounds.

The data depicted demonstrate that the products are present in nanocrystalline form in comparison with the fullerene. Such structures have not hitherto been described for simple fullerene-metal complexes.

Figure 2:
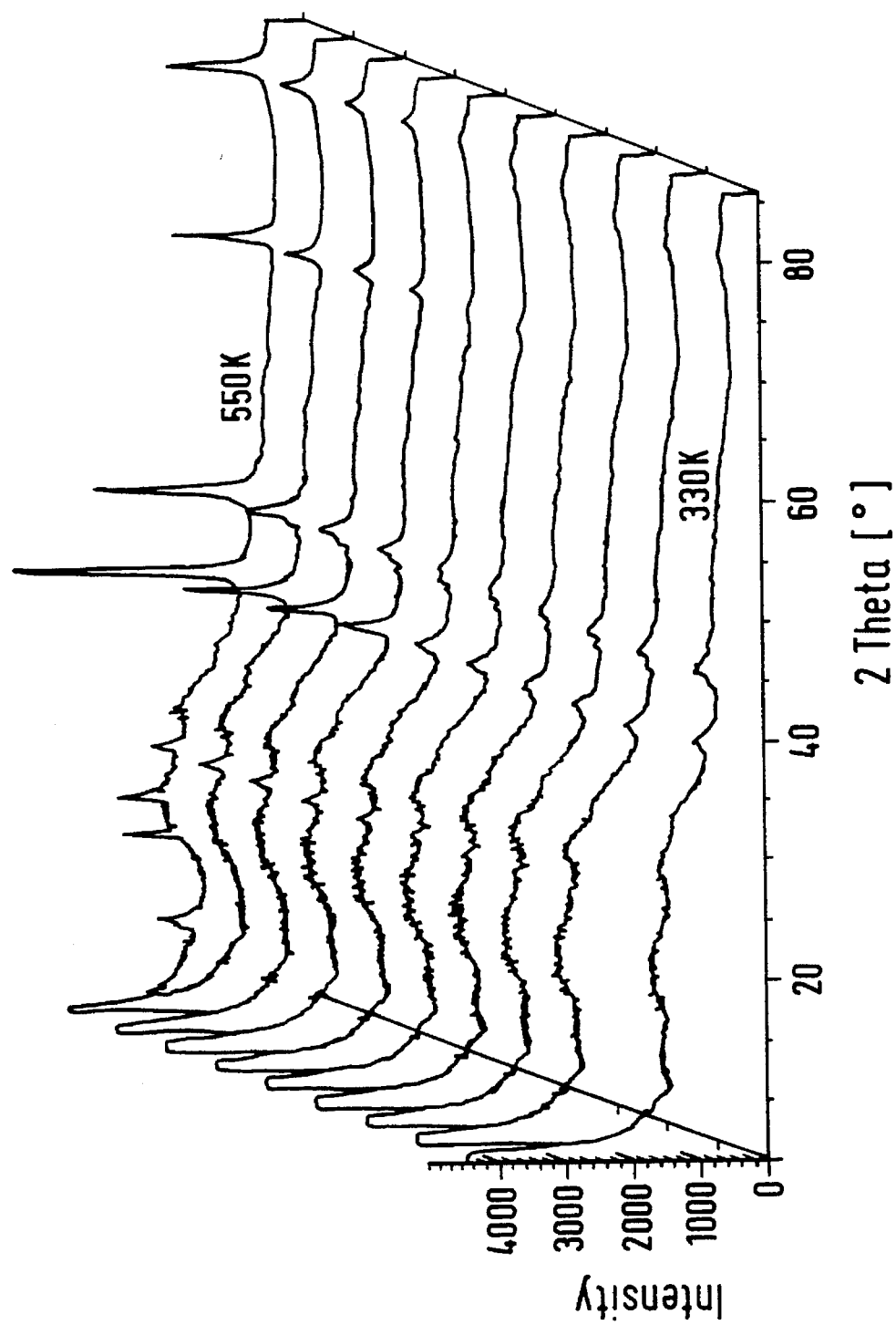

Further evidence for the assumed structure is the high-temperature XRD (Cu radiation) of the $Pd_3C_{60}$ compound (FIG. 2). On heating from 300 K. to 550 K., the compound decomposes into $C_{60}$ and elemental palladium. The spectrum (temperature intervals ≈30 K.) shows those skilled in the art a typical example of a de-intercalation reaction comparable with de-intercalation reactions of graphite intercalation compounds. Other transition metal-fullerene intercalation compounds undergo similar de-intercalation reactions.

The molecular structure of the intercalated transition metal compound has been able to be characterized in more detail by FT-IR spectra (FIG. 3). The spectra of the iron-fullerene and ruthenium-fullerene intercalation compounds show the presence of carbonyl ligands on the metal atoms. The splitting of the carbonyl bands is an index for the influence of the fullerenes on the transition metal atoms. The fullerene fingerprint pattern also changes accordingly.

The transition metal-fullerene intercalation compounds are particularly suitable as catalysts. Since the structural integrity of the material is maintained even under extreme reaction conditions, there are obtained particularly stable catalysts having a longer service lifetime than conventional catalysts. A substantial advantage in use in comparison with conventional metal-hydrocarbon catalysts is the targeted chemical anchoring of metals to the fullerene skeleton, which is made possible by the unique electronic structure of fullerene-type carbon skeletons. The metal-fullerene catalysts obtained can have their activity lastingly improved by promotors such as alkali metal compounds and heterocyclic organic compounds, as long as the promotors do not lead to destruction of the fullerene matrix.

Surprisingly, the transition metal-fullerene intercalation compounds of the invention additionally have high selectivity in the hydrogenation of compounds having a plurality of functional groups. Thus, for example, in an alkenal hydrogenation is predominantly of the carbonyl function rather than the C—C double bond.

EXAMPLE 1

Synthesis of $Pd_3$—$C_{60}$ $C_{60}$: 1.44 g (2 mmol)
$Pd(DBA)_2$: 3.45 g (6 mmol)
Toluene: 1000 ml The toluene was heated at reflux for 24 hours over metallic Na and freshly distilled. After complete dissolution of the $C_{60}$ in toluene, the palladium dibenzylideneacetone $(Pd(DBA)_2)$ complex was added all at once and the mixture was subsequently heated at the boiling point for 3 days under reflux. All the above work was carried out under argon (Schlenk tube technique).

After cooling the reaction solution to room temperature (under argon), the precipitate formed was filtered off with suction in air, washed with toluene, acetone and diethyl ether and subsequently dried overnight in vacuo.

Yield: 1.727 g of $Pd_3C_{60}$ (theoretical: 1.652 g)

EXAMPLE 2

Synthesis of $Pd_3$—$C_{60}$ $C_{60}$: 0.648 g (0.9 mmol)
$Pd(DBA)_2$: 1.55 g (2.7 mmol)
Toluene: 600 ml The toluene was heated at reflux for 24 hours over metallic Na and freshly distilled. After complete dissolution of the $C_{60}$ in toluene, the palladium complex was added all at once and the mixture was subsequently heated at the boiling point for 3 days under reflux. All the above work was carried out under argon (Schlenk tube technique).

After cooling the reaction solution to room temperature (under argon), the precipitate formed was filtered off with suction in air, washed with toluene and diethyl ether and subsequently dried overnight in vacuo.

Yield: 890 mg of $Pd_3C_{60}$ (theoretical: 743 mg)

EXAMPLE 3

Synthesis of $Ru_3$—$C_{60}$ $C_{60}$: 2161.9 mg (3 mmol)
$Ru_3(CO)_{12}$: 1918.0 mg (3 mmol)
Toluene: ca. 3000 ml Toluene was heated at reflux for 24 hours over metallic Na and freshly distilled. After complete dissolution of the $C_{60}$ in toluene, the ruthenium carbonyl was added all at once and the mixture was subsequently heated at the boiling point for 7 days under reflux. All the above work was carried out under argon (Schlenk tube technique). After cooling the reaction solution to room temperature (under argon), the precipitate formed was filtered off with suction in air, washed with toluene, and subsequently dried overnight in vacuo.

Yield: 3650 mg of $Ru_3C_{60}$

EXAMPLE 4

Synthesis of $Ru_x$-fullerene black

Fullerene black (not extracted): 3.5 g
$Ru_3(CO)_{12}$: 320 mg (0.5 mmol)=151.7 mg of Ru metal
Toluene: ca: 500 ml Toluene was heated at reflux for 24 hours over metallic Na and freshly distilled. The fullerene black and the ruthenium carbonyl were added successively to the toluene under argon and the mixture was subsequently heated at the boiling point for 7 days under reflux. All the above work was carried out under argon (Schlenk tube technique).

After cooling the reaction solution to room temperature (under argon), the precipitate formed was filtered off with suction in air, washed with toluene, and subsequently dried overnight in vacuo. The filtrate contained neither fullerenes nor Ru carbonyls.

EXAMPLE 5

Synthesis of $Ru_x$-fullerene black

Fullerene black (not extracted): 3.2 g
$Ru_3(CO)_{12}$: 320 mg (0.5 mmol)=151.7 mg of Ru metal
Toluene: ca. 500 ml Toluene was heated at reflux for 24 hours over metallic Na and freshly distilled. The fullerene black and the ruthenium carbonyl were added successively to the toluene under argon and the mixture was subsequently heated at the boiling point for 7 days under reflux. All the above work was carried out under argon (Schlenk tube technique).

After cooling the reaction solution to room temperature (under argon), the precipitate formed was filtered off with suction in air, washed with toluene, and subsequently dried overnight in vacuo. The filtrate still contained small amounts of higher Ru carbonyls.

EXAMPLE 6

Synthesis of $Pt_3$—$C_{60}$ $C_{60}$: 2161.9 mg (3 mmol)
$Pt_3(CO)_{12}$: 2763.8 mg (3 mmol)
Toluene: ca. 3000 ml The synthesis of $Pt_3C_{60}$ is carried out using the procedure of Example 3.

EXAMPLE 7

Preparation of Rh—$C_0$ Adduct 364.3 mg (0.342 mmol) of $Rh_6(CO)_{16}$ and 2.05 g (2.84 mmol) of $C_{60}$ are dissolved in 2 liters of toluene and irradiated for 7 hours with a mercury vapor lamp. The temperature of the solution varies within the range of 23°–29° C. After the reaction is complete, the mixture is evaporated to a volume of 500 ml and the precipitated black solid is filtered off.

Yield: 1.78 g

IR ($v$, cm$^{-1}$): 1540 (w), 1430 (vs, $C_{60}$), 1182 (s, $C_{60}$) 725 (w)

EXAMPLE 8

Synthesis of iron-$C_{60}$ Intercalation Compounds

A stoichiometric amount of $C_{60}$ and iron pentacarbonyl were dissolved in toluene and photochemically irradiated. The iron carbonyl-$C_{60}$ intercalation compound precipitated and was filtered off.

EXAMPLE 9

Use of $Pd_3$—$C_{60}$ as Hydrogenation Catalyst

The $Pd_3$—$C_{60}$ intercalation compound prepared in Example 1 (1 mol %) was stirred at 27° C. in tetrahydrofuran with cyclohexene and hydrogen (1 bar) until complete conversion had been achieved. The catalyst was filtered off and could be reused a number of times without loss in activity.

COMPARATIVE EXAMPLE 1

Use of Palladium on Activated Carbon as Hydrogenation Catalyst

Using the procedure of Example 9, cyclohexene was converted using palladium on activated carbon (Fluka) (1 mol %) in THF. After one conversion, the catalyst was no longer active.

EXAMPLE 10

Hydrogenation of 2-ethylhexenal 100 g of 2-ethylhexenal were hydrogenated in a stirring autoclave at 50 bar and 150° C. in the presence of 0.36 g of Ru—$C_{60}$ (0.1% of Ru), until the pressure no longer dropped. After 5 hours, the conversion was complete. The product mixture comprises 53.3 % of 2-ethylhexanol, 30.9 % of cis- and trans-2-ethylhexenol and 1% of 2-ethylhexanal.

COMPARATIVE EXAMPLE 2

100 g of 2-ethylhexenal were hydrogenated under the same experimental conditions as in Example 10 in the presence of Ru/C (No. 4855, Engelhard). After 3.5 hours, the hydrogenation activity was exhausted. The conversion is 80%. The product mixture comprises 31.85% of 2-ethylhexanol and 2-ethylhexenol, 26% of 2-ethylhexanal and 20% of starting material.

Example 10 shows the high selectivity of the catalyst of the invention for the formation of the unsaturated 2-ethylhexenols.

We claim:

1. A transition metal-fullerene intercalation compound.

2. A compound as claimed in claim 1, wherein the metals are selected from the group consisting essentially of Fe, Ru, Os, Co, Rh, Ir, Ni, Pd, and Pt.

3. A transition metal-fullerene intercalation compound wherein stabilizing ligands are additionally bound to the metals.

4. A compound as claimed in claim 3, wherein the ligand is a carbonyl ligand.

5. A compound as claimed in claim 3, wherein the ligand is a dibenzylideneacetone ligand.

6. A process for preparing transition metal-fullerene intercalation compounds which comprises reacting the transition metal compounds in a solvent with fullerene or fullerene-containing carbon black.

7. The process as claimed in claim 6, wherein the transition metal compounds used are in the oxidation state 0.

8. The process as claimed in claim 6, wherein the transition metal compounds used are transition metal carbonyls.

9. A method of using compounds as claimed in claim 2 as catalysts comprising the step of reacting at least one compound in the presence of said intercalation compound to result in a catalytic reaction.

10. A compound as claimed in claim 3, wherein the stabilizing ligands are selected from the group consisting of carbonyls, phosphines, arsines, olefins, alkynes, nitrogen, dibenzylideneacetone and aromatics.

11. The process as claimed in claim 6, wherein the solvent is an aromatic solvent.

12. The process as claimed in claim 11, wherein the aromatic solvent is selected from the group consisting of benzene, toluene, xylene, ethylbenzene, chlorobenzene, dichlorobenzene, carbon tetrachloride, chloroform, dichloromethane and furan.

13. The process as claimed in claim 6, wherein the step of reacting is carried out at a temperature of from −40° to 250° C.

14. The process as claimed in claim 12, wherein the step of reacting is carried out at a temperature of from 0° to 200° C.

15. The process as claimed in claim 6, wherein the step of reacting is carried out under a pressure of from 1 to 100 atmospheres.

16. The process as claimed in claim 15, wherein the step of reacting is carried out under a pressure of from 1 to 10 atmospheres.

17. The process as claimed in claim 6, wherein the step of reacting is carried out photochemically.

18. A compound as claimed in claim 2, wherein the metals are selected from the group consisting essentially of Fe, Rh, Pd, Ru and Pt.

19. The process as claimed in claim 6, wherein the step of reacting is carried out from 6 to 72 hours.

20. A transition metal-fullerene intercalation compound wherein the transition metals are selected from the group consisting of transition metal compounds in the oxidation state 0 and those transition metal compounds that can be reduced to an oxidation state 0.

21. A transition metal-fullerene intercalation compound made according to the process as claimed in claim 6.

* * * * *